United States Patent [19]

Moore et al.

[11] Patent Number: 4,752,578
[45] Date of Patent: Jun. 21, 1988

[54] COLLAGENASE INDUCING FACTOR

[75] Inventors: William M. Moore, St. Charles; Curtis A. Spilburg, Chesterfield, both of Mo.

[73] Assignee: Monsanto Company, St. Louis, Mo.

[21] Appl. No.: 851,039

[22] Filed: Apr. 11, 1986

[51] Int. Cl.$^4$ .......................... C12P 21/00; C12P 1/00; C12N 9/64

[52] U.S. Cl. ........................................ 435/68; 435/41; 435/226

[58] Field of Search ............................ 435/226, 68, 47

[56] References Cited

U.S. PATENT DOCUMENTS 4,209,587  6/1980  Tolbert et al. .................... 435/41
4,289,854  9/1981  Tolbert et al. .................... 435/41

OTHER PUBLICATIONS

Fogh and Trempe, "New Human Tumor Cell Lines" in Human Tumor Cell Lines In Vitro (Fogh ed.), 1975, Plenum Publ. Corp., N.Y., pp. 115-159.

Fogh et al., J. Natl. Cancer Inst., 58, 209-214, 59, 221-226, (1977).

American Type Culture Collection Catalogue of Strains II, Fourth Ed. 1983, p. 175.

Moscatelli et al., Exper. Cell Res. 156, 379-390 (1985).

Doyle et al., Biochem. Biophys. Res. Commun. 130(2), 768-773 (1985).

*Primary Examiner*—Lionel M. Shapiro
*Attorney, Agent, or Firm*—Scott J. Meyer; James W. Williams, Jr.

[57] ABSTRACT

A method for the production of collagenase inducing factor is disclosed which comprises growing the human liver adenocarcinoma cell line SK-HEP-1 in nutrient culture medium at 35°-38° C. and recovering the resulting collagenase inducing factor from the spent cells or conditioned medium.

3 Claims, No Drawings

COLLAGENASE INDUCING FACTOR

BACKGROUND OF THE INVENTION

This invention relates to the in vitro production of collagenase inducing factor from the human liver adenocarcinoma cell line SK-HEP-1.

Collagenase is a proteolytic enzyme which acts on the protein collagen. The natural substrate collagen constitutes the connective tissue of the body and is the major type of fibrous protein in higher vertebrae, including mammals. In man, approximately one-third of the total protein content is collagen. The ability of collagenase to digest native collagen provides the enzyme with a variety of uses in tissue culture and cell studies including the isolation of tissue collagen and other types of tissue dissociation.

Collagenase also is believed to be associated with the tissue invasion progress in tumor angiogenesis, in arthritic conditions such as rheumatoid arthritis, in corneal ulceration, osteoporosis, and other diseases of connective tissue. It has been suggested that tumor angiogenesis factor (TAF) induces collagenase secretion by blood vessel endothelial cells. See Moscatelli et al., Cell 20, 343 (1980).

Rheumatoid arthritis is an inflammatory disease of the joints and connective tissue, leading to the proteolytic degradation of articular cartilage which eventually results in loss of normal joint function. The source of this destructive hydrolytic activity is the synovial cell, the primary cell lining the joint capsule. Under the stimulus of an immune reaction, proteolytic enzymes, especially collagenase, are synthesized by this cell and secreted into the joint. This high level of proteolytic activity gives rheumatoid synovium invasive capabilities which are similar to those of a malignant tumor.

The prominent role of collagenase in the degradation of the joint thus provides an important nexus for scientific investigation and the application of studies for therapeutic intervention in degenerative diseases.

BRIEF DESCRIPTION OF THE INVENTION

In accordance with the invention a collagenase inducing factor (CIF) is isolated from the human liver adenocarcinoma cell line SK-HEP-1. It has been found that the SK-HEP-1 cells contain a messenger molecule, CIF, which signals the synovial cells to synthesize collagenase.

The established cell line SK-HEP-1 was derived from a liver adenocarcinoma by G. Trempe of Sloan-Kettering Institute for Cancer Research in 1971, and cultures of the cell line are available from that institute. The SK-HEP-1 cell line also is on deposit without restriction in the permanent collection of the American Type Culture Collection, Rockville, Maryland, under accession number ATCC HTB 52. Samples of the cell line can be obtained by the public upon request to that depository.

The establishment and characterization of the SK-HEP-1 cell line is well-known and published as follows:

Fogh and Trempe, "New Human Tumor Cell Lines" in *Human Tumor Cells In Vitro* (Fogh. ed.), Plenum Publ. Corp., New York, 1975, pp. 14 115–159;

Fogh et al., *J. Nat'l. Cancer Inst.*, 58, 209–214 (1977); Ibid; 59, 221–226 (1977); and Natl. Cancer Inst. Monogr. 49, 5–19 (1978).

The SK-HEP-1 cell line also is known to be useful for the production of human tumor angiogenesis factor (TAF) as described in U.S. Pat. No. 4,209,587.

In accordance with this invention, the CIF has been purified from the SK-HEP-1 conditioned media and from the SK-HEP-1 cell extracts or lysates.

The CIF has a molecular weight of about 18,000 and has been shown to stimulate synovial cell collagenase and prostaglandin $E_2$ (PGE$_2$) synthesis. These properties of CIF are similar to the properties of interleukin 1.

DETAILED DESCRIPTION OF THE INVENTION

As is known from U.S. Pat. Nos. 4,209,587 and 4,289,854, the SK-HEP-1 cells grow rapidly in suspension culture and large amounts of spent media or cells can be generated in a short time. According to the present invention, using SK-HEP-1 conditioned media, CIF was substantially purified to homogeneity using a four step procedure consisting of ammonium sulfate fractionation, Affi-Gel® Blue chromatography, Bio-Gel® HTP chromatography and Sephadex® G-75 gel filtration chromatography.

SK-HEP-1 cells also were harvested from the cell culture by separation from the conditioned media and then used as a source of the CIF. Thus, the CIF was purified from the cell lysate obtained by freezing and thawing the cells suspended in low ionic strength buffer. The cell extracts were passed over a PBE® 94 chromatofocusing column and the peaks of activity obtained with isoelectric points ranging from about pH 4.0 to 5.1 were combined into four major pools. Then, following Phenyl-Sepharose CL-4B chromatography, the pools were purified to very high specific activity by gel filtration on Bio-Gel P-30.

Maintenance and growth of the SK-HEP-1 cells for production of CIF can be had in Dulbecco's modified Eagle'medium (DMEM) or other conventional nutrient culture media, preferably fortified with 5–15% fetal bovine serum (FBS). Suitable growth of the cells can be carried out at about 35°–38° C. but cell proliferation is best at 37° C. Propagation of the cells can be had in conventional cell culture apparatus such as roller bottles, T-flasks, spinner flasks and larger agitated suspension vessels.

The chromatography materials used for the purification of the CIF from the conditioned media or the cell lysates are well-known, commercially available products. Thus, Affi-Gel Blue is a beaded affinity chromatography gel support bed consisting of a N-hydroxysuccinimide ester of a derivatized cross-linked agarose covalently attached to Cibacron® Blue F3GA dye. It has 2 mg of the dye per ml of gel and is commercially available from Bio-Rad Laboratories, Richmond, California.

Bio-Gel HTP is a hydroxyapatite (a form of calcium phosphate) chromatography gel and Bio-Gel P-30 is a polyacrylamide gel filtration gel, both of which are also commercially available for Bio-Rad Laboratories.

Sephadex G-75 is a cross-linked dextran gel filtration material in bead form prepared by cross-linking dextran with epichlorohydrin. It is commercially available from Pharmacia Fine Chemicals AB, Uppsala, Sweden.

Phenyl-Sepharose CL-4B is a cross-linked agarose affinity chromatography gel coupled to a phenyl group through a glycidyl ether linkage. It is also commercially available from Pharmacia Fine Chemicals.

Polybuffer exchangers (PBE) are bead-formed exchanger gels used with Polybuffers, both of which are commercially available for chromatofocusing by Pharmacia Fine Chemicals.

The following examples will further illustrate the invention although it will be appreciated that the invention is not limited to these specific examples.

EXAMPLE 1

SK-HEP-1 Cells: One vial of frozen SK-HEP-1 cells was rapidly thawed in a 37° C. water bath, the contents transferred to a 75 cm$^2$ T-flask and 25 ml of DMEM containing 10% FBS added. The flask was incubated at 37° C. in an atmosphere containing 6–8% $CO_2$. After one day, the media was changed to remove the last traces of the freezing media and four days later the cells were washed with 25 ml phosphate buffered saline (PBS) containing 0.02% ethylene diamine tetracetate (EDTA). Five ml of the same media were added and the cells were removed with gentle tapping. Five 75 cm$^2$ T-flasks were inoculated with 1 ml of cells and 25 ml of DMEM+10% FBS were added. For suspension culture, a 500 ml spinner flask was inoculated with cells from five 75 cm$^2$ T-flasks and sufficient DMEM+10% FBS added to bring the volume to 500 ml. The media was harvested three times per week by pouring off 400–450 ml and leaving 50–100 ml for reinoculation. The spinner was maintained in a $CO_2$ incubator at 37° C. with 6–8% $CO_2$.

Purification of CIF from SK-HEP-1 Conditioned Media. SK-HEP-1 conditioned media was harvested from cells grown either in T-Flasks or in 500 ml spinner flasks and stored frozen until ready for use. The frozen media from several harvests was thawed, pooled and filtered (0.2μ). Preliminary tests indicated that an ammonium sulfate concentration of 55% of saturation was sufficient to precipitate almost all of the activity but only part of the total protein. In a typical preparation 2118 ml of pooled conditioned media were made to 55% of saturation of ammonium sulfate by the addition of 743 grams of the solid with stirring for one hour at room temperature. The resulting precipitate was collected by centrifugation at 11,600×g for 30° C. minutes at 4° C. The precipitate was dissolved in water and dialyzed (3500 mol. wt. cutoff) against 55 liters of water in the cold room over 24 hours with at least two changes. A small precipitate was removed from the dialyzed solution by centrifugation to yield 205 ml of a clear, amber solution. This solution was made 0.05 M in sodium phosphate, pH 6.0, by addition of 0.5 M sodium phosphate and applied to an Affi-Gel Blue column (5.0×40 cm) equilibrated in 0.05 M sodium phosphate, pH 6.0. The column was eluted with column buffer at a flow rate of 107 ml/hr and 27 ml fractions collected. Fractions were measured for activity and $A_{280}$. Affi-Gel Blue chromatography results in a large fraction of the protein eluting in a major peak and then gradually trailing off with continued elution. The CIF activity is noticeably retained and elutes from the column after the main protein fraction in a broad band, indicative of multiple peaks of activity.

Active fractions 65–160 were pooled and applied to a column of Bio-Gel HTP (2.6×15 cm) equilibrated with 0.05M sodium phosphate, pH 6.0, at a flow rate of 50 ml/hr. The column was washed until the absorbance at 280 nm returned to baseline and was then eluted with a 600 ml linear gradient from 0.05 M to 0.30M sodium phosphate, pH 6.0. Ten ml fractions were collected. The Bio-Gel HTP column bound and concentrated the activity from the Affi-Gel Blue pool and also gave a further increase in purification.

The active fractions from Bio-Gel HTP were pooled, dialyzed against water and lyophilized. The lyophilized material was dissolved in 0.05 M sodium phosphate, pH 7.5, 0.5 M sodium chloride and dialyzed against the same buffer containing 10% sucrose to concentrate the sample to a volume of 4 ml. This sample was then applied to a Sephadex G-75 Superfine column (2.6×94 cm) and eluted with the dialysis buffer (minus sucrose) at a flow rate of 13 ml/hr. Four ml fractions were collected and measured for $A_{280}$ and activity. Almost all of the protein eluted from the column near the void volume while the active fraction appeared at a retention volume corresponding to a molecular weight of 13,000–19,000.

The summary of the purification scheme is shown in Table 1. Each step resulted in a significant increase in specific activity with an overall yield of about 5%. The final gel filtration step resulted in a fraction with very high specific activity and essentially immeasurable absorbance (<0.001) at 280 nm. As a result of this low level of material, a precise value for specific activity is difficult to define.

TABLE 1

| PURIFICATION OF CIF FROM SK-HEP-1 CONDITIONED MEDIA | | | | |
|---|---|---|---|---|
| STEP | VOLUME (ml) | PROTEIN ($A_{280}$) | ACTIVITY, U ($PGE_2$ μg/18 hrs) | SPECIFIC ACTIVITY ($U/A_{280}$) |
| SK-HEP-1 (CONDITIONED MEDIA) | 2118 | — | 555 | — |
| 0–55% AMMONIUM SULFATE | 227 | 1866 | 527 | .28 |
| AFFI-GEL BLUE | 3240 | 379 | 262 | .69 |
| BIO-GEL HTP | 205 | 26 | 152 | 5.8 |
| G-75 SEPHADEX | 36 | ~0.07 | 28 | ~400 |

Purification of CIF from SK-HEP-1 Cell Lysates: When SK-HEP-1 conditioned media was harvested from cells grown in a spinner flask, a considerable number of cells was also obtained. Preliminary tests indicated that when cells were frozen with the media, at least two-fold higher levels of CIF activity were obtained compared to freezing the media with the cells removed. Effective release of CIF was obtained by freezing and thawing cells suspended in low ionic strength buffer.

Based on these observations, SK-HEP-1 cells were preferably used as a starting material rather than conditioned media. Using cells as the starting material eliminated the large, initial volumes of conditioned media since 1–3 mls of packed cells had about the same activity as one liter of media. This also had the advantage of providing a starting sample free of serum protein, a major source of impurities.

SK-HEP-1 cells were harvested several times each week from 500 ml spinner flasks by centrifugation of the media at 900×g for 20 minutes. The cells were resuspended in 50 ml of phosphate buffered saline (PBS), recentrifuged and the supernatant was discarded. This washing step was then repeated. Washed cells were suspended in 0.025 M histidine-HCl, pH 5.9, and frozen. The cell suspension (3-5 ml) was thawed and centrifuged for 30 minutes at 30,000×g to obtain the supernatant. This freezing and thawing released almost all of the CIF activity from the cells. The supernatant fraction was dialyzed against 0.025 M histidine-HCl, pH 5.9, and applied to a column of Polybuffer Exchanger 94 (1.0×35 cm), Pharmacia Inc., previously equilibrated with the same buffer. The pH gradient was developed by elution with 350 ml of Polybuffer 74 (diluted 1:8 with water and titrated to pH 4.0 with HCl). After collection of 70 fractions (5.0 ml), the column was eluted with a 100 ml linear gradient from 0 to 1.0 M sodium chloride in Polybuffer 74, pH 4.0. Fractions were measured for pH, $A_{280}$ and CIF activity.

Chromatofocusing resulted in the separation of CIF activity into at least four major peaks with high specific activity. These peaks were pooled separately to give 4 fractions with approximate isoelectric points corresponding to 5.1, 4.7, 4.0 and <4 and labeled P1, P2, P3 and P4, respectively. These fractions were treated identically throughout the rest of the procedure. Each pooled fraction was made to 0.8 M in ammonium sulfate by the addition of a solution of saturated ammonium sulfate (pH 7) and applied to a 1.0 ml column of Phenyl-Sepharose Cl-4B equilibrated in 0.01 M sodium phosphate, pH 6.8, and 0.8 M ammonium sulfate. After applying the sample, the column was washed with 3-4 column volumes of buffer to ensure that all of the Polybuffer 74 had been removed. Essentially all of the activity was bound to the column. The column was then eluted with 4 ml of 40% ethylene glycol in 0.01 M sodium phosphate, pH 6.8. The fraction obtained was dialyzed exhaustively against water, and activity and $A_{280}$ determined. Each fraction was then dialyzed against 0.05 M sodium phosphate, pH 6.0, 0.5 M sodium chloride containing 10% sucrose to concentrate the sample and applied to a Bio-Rad P-30 gel filtration column (1.6×94 cm). Two ml fractions were collected and samples were tested for activity. Fractions P1, P2, and P3 each eluted in the same position as a single sharp peak with a molecular weight corresponding to ~19,000. Fraction P4 eluted in a broader peak corresponding to a peak at ~19,000 and one at ~13,000 MW. While activity was easily measured in the synovial $PGE_2$ assay, the absorbance at $A_{280}$ and at $A_{220}$ were very low and essentially the same as background, indicating a very high specific activity for each peak, and a very small amount of material. A summary of the purification scheme is shown in Table 2 and indicates a substantial purification with a yield of around 5-10%.

TABLE 2

| PURIFICATION OF CIF FROM SK-HEP-1 CELL LYSATES | | | | |
|---|---|---|---|---|
| | VOLUME (ml) | PROTEIN ($A_{280}$) | ACTIVITY, U ($\mu$g $PGE_2$/18 hrs.) | S.A. U/$A_{280}$ |
| CELL LYSATE | 48.5 | 118 | 555 | 4.7 |
| CHROMATOFOCUSING | | | | |
| POOL 1 | 50 | 3.35 | 137 | 41 |
| POOL 2 | 59.5 | 3.21 | 168 | 52 |
| POOL 3 | 51.5 | 2.0 | 142 | 71 |
| POOL 4 | 36.5 | 21.9 | 491 | 22 |
| PHENYL-SEPHAROSE | | | | |
| POOL 1 | 11.5 | 1.33 | 137 | 103 |
| POOL 2 | 12 | 1.31 | 61 | 47 |
| POOL 3 | 12 | 0.47 | 48 | 102 |
| POOL 4 | 11.5 | 2.57 | 199 | 77 |
| BIO-RAD P-30 | | | | |
| POOL 1 | 10 | ~0.02 | 8.2 | ≧410 |
| POOL 2 | 10 | ~0.01 | 11.0 | ≧1100 |
| POOL 3 | 10 | ~0.04 | 13.3 | ≧330 |
| POOL 4 | 14 | ~0.04 | 34.7 | ≧860 |

EXAMPLE 2

CIF as produced in Example 1 was tested for stimulation of synovial cell collagenase and $PGE_2$ synthesis as follows:

$^{14}$-Collagen: $^{14}$C-collagen was prepared by reductive methylation of calf skin collagen using $^{14}$C-formaldehyde and sodium borohydride. Calf skin collagen (Sigma) was dissolved at 7.5 mg/ml in 60 ml of 0.10 M acetic acid and dialyzed at 4° C. against 0.15M potassium phosphate, pH 7.6, for eight hours followed by dialysis overnight against 0.40M NaCl. The collagen solution was then adjusted to pH 9.0 by addition of 0.50M sodium borate and then 1 mCi of $^{14}$C-formaldehyde was added. After 1 minute, 0.10 M sodium borohydride (660 $\mu$l in 1.3 mM NaOH) was added in four aliquots, followed by an additional aliquot (340 $\mu$l) 30 minutes later. The solution was then dialyzed exhaustively against 0.01M acetic acid, centrifuged to remove particulates and stored frozen in 1 ml aliquots. Specific activity was $1.3 \times 10^6$ DPM/mg. Unlabeled collagen was prepared in the same way, stored frozen and mixed with labeled collagen at a ratio of 9 to 1.

Collagenase Assay: $^{14}$C-collagen was dialyzed 6-8 hours at 4° C. against 0.15M NaCl/potassium phosphate, pH 7.6, followed by dialysis overnight against 0.4M sodium chloride. This solution was centrifuged to remove any undissolved collagen and stored at 4° C. The assay was performed in 1.5 ml polypropylene microfuge tubes. Each assay tube contained 50 $\mu$l of 1.0 M $^{14}$C-collagen solution (4 mg/ml) and 50 $\mu$l of 1.0M glucose, 0.10 M Tris, 0.4 M NaCl, 0.02 M $CaCl^2$, pH 7.5. This solution was incubated for ten minutes at 35° C. and the reaction initiated by the addition of 100 $\mu$l of enzyme solution. Those samples containing procollagenase were first activated by incubating 100 $\mu$l aliquots with 1-5 $\mu$l of 10 mg/ml trypsin (in 1 mM HCl) for 20 minutes at 23° C., followed by 20 μl of 5 mg/ml soybean trypsin inhibitor (in 0.05M Tris, 0.01M $CaCl_2$, pH 7.5) to quench the trypsin activity. The collagenase assay was terminated after 30 minutes at 35° C. by the addition of 20 μl of 0.08M 1,10-phenanthroline in 50% (v/v) dioxane and the incubation was continued for one hour at 35° C. to denature the collagen digestion products. Each sample was cooled for 15 minutes at 23° C. and 200 μl of dioxane added with vigorous vortexing to precipitate uncleaved collagen. Following centrifugation at 11,000 RPM, 350 μl aliquots were added to 5.0 ml of Pico-Fluor 30 to determine radioactivity.

Isolation of Synovial Cells: Approximately 2.0 grams of synovial tissue were obtained from a middle-age female undergoing synovectomy of the knee. All procedures were carried out in a laminar flow hood under aseptic conditions. The tissue was placed in 250 ml McCoys 5 A (modified) medium containing 200 ml gentamicin and stored overnight at 0° C. The next day the tissue was warmed to room temperature, cut into 0.25 cm pieces and added to 11 ml of serum free Dulbecco's modified Eagle's medium (DMEM), containing 4 mg/ml clostridial collagenase (Worthington). After incubating the mixture for one hour at room temperature, an equal volume of 0.25% trypsin was added and the incubation continued for an additional thirty minutes. The cells were spun down at 400×g for ten minutes, resuspended in 20 ml trypsin/EDTA (Gibco 10X) and incubated for 30 minutes with occasional mixing by drawing through a 25 ml pipet. The suspension was centrifuged and the pellet washed two times with PBS:DMEM (1:1) containing 10% fetal bovine serum (FBS). The cells were resuspended at $1 \times 10^6$ cells/ml in DMEM containing 10% FBS and 100 μg gentamicin. After incubating overnight at 37° C. in a $CO_2$ incubator (5–8% $CO_2$), the non-adherent cells were aspirated off and the adherent cells were washed with PBS:DMEM (1:1) containing 10% FBS, followed by DMEM containing 10% FBS+100 μg/ml gentamicin and finally with DMEM containing only 10% FBS. At the first passage, the original T-flask was split one to four.

$PGE_2$/Synovial Cell Assay: Samples to be assayed were diluted with fresh culture media (DMEM+10% FBS) to a volume of 5 ml, sterile filtered and applied to confluent human synovial cells grown in 16 mm wells. For each sample, 1 ml was added to each of 4 wells. After 18 hours at 37° C. the media was removed, diluted appropriately and assayed for $PGE_2$ content using a $^{125}$I RIA kit from New England Nuclear. The data were reported in terms of the $PGE_2$ produced.

Collagenase/Synovial Cell Assay: Samples to be assayed for their ability to stimulate collagenase production by synovial cells were diluted with fresh culture media (DMEM+10% FBS), sterile filtered and applied to confluent cells in 16 mm wells as described for the $PGE_2$ assay. The samples were removed at one to three day intervals and fresh sample applied to the cells. Aliquots were then assayed using the soluble collagen substrate assay described in detail above.

Stimulation of Synovial Cell Collagenase and $PGE_2$ Synthesis by SK-HEP-1 Conditioned Media. The initial observation that tumor conditioned media stimulates synovial cells to produce collagenase was obtained by feeding confluent synovial cells with SK-HEP-1 cell conditioned media. This media was changed at three or four day intervals and aliquots taken for collagenase assays. As seen in runs (a) and (b) of Table 3, substantial collagenase activity appeared after day three or day six, respectively, and continued to increase thereafter. Control cells treated only with culture media gave no activity. When SK-HEP-1 conditioned media was tested for its effect on synovial cell $PGE_2$ production, a dramatic rise of $PGE_2$ levels was observed over a period of 24 hours (Table 4) after which the values reached a plateau. Because of the rapid response of synovial $PGE_2$ production to tumor conditioned media, this response became the basis of a routine assay for monitoring the purification of CIF. A plot of $PGE_2$ produced over a period of 18 hours versus mls of added SK-HEP-1 conditioned media resulted in a linear response.

TABLE 3
STIMULATION OF SYNOVIAL CELL COLLAGENASE SYNTHESIS BY SK-HEP-1 CONDITIONED MEDIA

| Run (a) | | Run (b) | |
|---|---|---|---|
| DAY | ACTIVITY (DPM) | DAY | ACTIVITY (DPM) |
| 0 | 0 | 0 | 0 |
| 3 | 633 | 3 | 42 |
| 6 | 1049 | 6 | 3022 |
| 10 | 3105 | 10 | 2355 |
| 13 | 2394 | 13 | 2178 |
| 17 | 3574 | | |

TABLE 4
STIMULATION OF SYNOVIAL CELL $PGE_2$ SYNTHESIS BY SK-HEP-1 CONDITIONED MEDIA

| | $PGE_2$ (pgm/0.1 ml) | |
|---|---|---|
| | CONTROL | +SK-HEP-1 |
| TIME (HRS) | | |
| 0 | <1 | 4 |
| 1½ | <1 | 18 |
| 3 | 23 | 87 |
| 4 | 67 | 438 |
| 8 | 375 | 6470 |
| 24 | 528 | 90,600 |
| TIME (DAYS) | | |
| 0 | 2 | 5 |
| 1/6 | 74 | 1500 |
| 1 | 626 | 59,400 |
| 4 | 1081 | 58,900 |

The foregoing examplary results confirm the desirable properties of the messenger molecule, collagenase inducing factor (CIF), obtained from the SK-HEP-1 cells. The isolated CIF also was found useful in inducing bone resorption of mouse calvaria and in stimulating the proliferation of mouse thymocytes. Similarity with interleukin-1 (IL-1) was observed by producing antibodies to a mixture of IL-1α and IL-1β in rabbits and finding that the antibodies were able to inactivate not only IL-α and IL-1β activity but also CIF activity.

Various other examples will be apparent to the person skilled in the art after reading the present disclosure without departing from the spirit and scope of the invention, and it is intended that all such other examples be included within the scope of the appended claims.

What is claimed:

1. Method for the production of collagenase inducing factor that stimulates synthesis of synovial cell collagenase and prostaglandin $E_2$ comprising growing the human liver adenocarcinoma cell line SK-HEP-1 in nutrient culture media at 35°–38° C. and recovering the resulting collagenase inducing factor from the spent cells or conditioned medium.

2. The method of claim 1 in which the collagenase inducing factor is recovered from the spent cells by freezing and thawing said cells suspended in low ionic buffer followed by subjecting the resulting cell lysate to the stepwise sequence of chromatofocusing with Polybuffer exchanger, Phenyl-Sepharose chromatography, and Bio-Gel P-30 gel filtration chromatography.

3. The method of claim 1 in which the collagenase inducing factor is recovered from the conditioned medium by the stepwise sequence of ammonium sulfate fractionation, Affi-Gel Blue chromatography, Bio-Gel HTP chromatography, and Sephadex G-75 gel filtration chromatography.

* * * * *